United States Patent
Humblot et al.

(10) Patent No.: US 11,046,631 B2
(45) Date of Patent: Jun. 29, 2021

(54) DIPHENOL AND PHENOL PRILLS AND METHOD FOR OBTAINING THE SAME

(71) Applicant: RHODIA OPERATIONS, Paris (FR)

(72) Inventors: Cédric Humblot, Lyons (FR); David Vanzin, Franklin, TN (US); Lars Fischer, Vienne (FR); Rodolphe Sapey-Triomphe, Serezin-du-Rhone (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 16/486,427

(22) PCT Filed: Feb. 21, 2018

(86) PCT No.: PCT/EP2018/054272
§ 371 (c)(1),
(2) Date: Aug. 15, 2019

(87) PCT Pub. No.: WO2018/153913
PCT Pub. Date: Aug. 30, 2018

(65) Prior Publication Data
US 2020/0031749 A1 Jan. 30, 2020

Related U.S. Application Data

(60) Provisional application No. 62/461,530, filed on Feb. 21, 2017.

(51) Int. Cl.
C07C 37/70 (2006.01)
C07C 39/04 (2006.01)
(Continued)

(52) U.S. Cl.
CPC ............... *C07C 37/70* (2013.01); *B01J 2/02* (2013.01); *B01J 2/20* (2013.01); *C07C 39/04* (2013.01); *C07C 39/06* (2013.01); *C07C 39/08* (2013.01)

(58) Field of Classification Search
None
See application file for complete search history.

(56) References Cited

U.S. PATENT DOCUMENTS 4,740,634 A 4/1988 Gomes de Matos et al.
7,235,299 B2 * 6/2007 Le Thiesse ............ C07C 46/10
428/402
(Continued)

FOREIGN PATENT DOCUMENTS

JP H06107580 A 4/1994
JP H06107581 A 4/1994
(Continued)

*Primary Examiner* — Medhant W Bahta

(57) ABSTRACT

The invention relates to a novel solid form of diphenol compound. A process for the preparation of diphenol prills having a spherical shape is disclosed. Said process comprising providing a molten composition comprising from 50 to 100 wt. % of a diphenol compound or a mixture of at least two diphenol compounds, and less than 0.1 wt. % of water; forcing said molten composition through at least one droplet generator means to form droplets; and cooling said droplets to form solid diphenol prills. The diphenol prills obtainable by said process are also one subject-matter of the invention.

15 Claims, 2 Drawing Sheets

(51) Int. Cl.
  *C07C 39/06* (2006.01)
  *C07C 39/08* (2006.01)
  *B01J 2/02* (2006.01)
  *B01J 2/20* (2006.01)

(56) References Cited

U.S. PATENT DOCUMENTS 8,071,817 B2  12/2011  Gayet et al.
8,557,380 B2  10/2013  Le Thiesse

FOREIGN PATENT DOCUMENTS

| JP | 2000302716 A | 10/2000 |
| WO | 0170869 A2 | 9/2001 |
| WO | 2004/039758 A1 | 5/2004 |
| WO | 2008/000955 A1 | 1/2008 |
| WO | 2008000956 A1 | 1/2008 |
| WO | 2016033157 A1 | 3/2016 |

* cited by examiner

DIPHENOL AND PHENOL PRILLS AND METHOD FOR OBTAINING THE SAME

This application is a U.S. national stage entry under 35 U.S.C. § 371 of International Application No. PCT/EP2018/054272 filed 21 Feb. 2018, which claims priority to U.S. Provisional Application No. 62/461,530 filed on 21 Feb. 2017. The entire content of each of these applications is hereby incorporated herein by reference.

TECHNICAL FIELD OF THE INVENTION

The present invention relates to a novel solid form of diphenol compound. More particularly, the invention provides a new method for preparing diphenol prills having a spherical shape. The invention also relates to said diphenol prills obtained by said new method.

BACKGROUND OF THE INVENTION

Among diphenol compounds, hydroquinone (HQ) is a product that is widely used in many fields as antioxidant in elastomers, polymerization inhibitor or as a monomer for polymer production. Thus, it is a product that is used in large quantities.

Currently, hydroquinone is commercially available in different forms, mainly as crystal powder. For instance, the patent document WO 2016/033157 discloses methods for making powders of crystallized hydroquinone particles and methods for making the same are provided. However, the powder is formed of small and brittle needles. The disadvantages which result therefrom are the presence of fines, which cause problems of dust formation during storage, transportation and physical handling and movement of said powder. Even with reduced agglomeration tendencies, hydroquinone powders may still be dangerous to the environment and individuals because of the risks of explosion and because this substance is an irritant for the eyes and the respiratory tract and can also cause skin irritation on contact.

Alternative forms have been disclosed.

Japanese patent JP 2000-302716 A discloses a technique for granulating hydroquinone, which consists of passing hydroquinone powder between two rolls to produce tablets, then crushing the tablets to obtain granules. The disadvantage of that process is that dust can subsist in the granulated product either because of the passage through the rollers, breaking the crystals in the rollers of the compacter, or by wear of the tablets in the crusher. Further, the granules are compact and their rate of dissolution is very low compared with the initial powder. Additionally, the granules may cake or clump upon storage and be difficult to process and transport in processing equipment. The granules may also be prone to attrition during handling.

The patent document WO 01/70869 discloses the preparation of granules of at least one sterically hindered phenol antioxidant using an organic processing agent. Said organic processing agent is mixed with said antioxidant to form a paste, which is processed to form granules, and said granules are finally dried to remove the organic processing agent without melting the antioxidant. One problem of this method is that the final antioxidant granules may still comprise some undesired traces of the organic processing agent.

The patent documents WO 2008/000955 & WO 2008/00956 discloses a hydroquinone in flake form, and process for obtaining it.

The patent document WO 04039758 discloses hydroquinone beads (also called "pearls"), which are highly spherical solid particles. These hydroquinone beads are said to be devoid of dust and have a physical form which confers on them good resistance to attrition. The process for the preparation of said beads consists in preparing, under hot conditions, a concentrated aqueous solution of hydroquinone, in then fragmenting the solution into droplets by passing through a nozzle and in cooling the droplets obtained in a gas stream so that they solidify to give beads which are subsequently recovered and dried. Because the first step of this process consists in dissolving hydroquinone in water, the obtained beads comprises typically between 10 and 50% of water before drying, and still between 0.1 and 1% water after the drying step. The residual presence of water may be a problem since, for some applications, the market requires water-free compounds.

Other diphenol compounds, like pyrocatechol compounds, are of high interest as well.

The present invention aims to provide a novel presentation of a phenolic compound, in particular hydroquinone, to overcome said disadvantages, and that offers improved handling and flowability and reduces safety, health and environmental risk to both personnel and the environment by minimizing dust and fines.

SUMMARY OF THE INVENTION

One subject-matter of the present invention is a new form of diphenol compounds.

More specifically, the invention relates to a process for the preparation of diphenol prills, said process comprising:
 providing a molten composition comprising from 50 to 100 wt. %, preferably from 75 to 100 wt. % and more preferably from 90 to 100 wt. %, of a diphenol compound or a mixture of at least two diphenol compounds, and less than 0.1 wt. % of water;
 forcing said molten composition through at least one droplet generator means to form droplets;
 cooling said droplets to form solid diphenol prills.

The diphenol prills obtainable by said process are also one subject-matter of the present invention.

Additionally, the invention relates to diphenol prills comprising from 50 to 100 wt. %, preferably from 75 to 100 wt. %, and more preferably from 90 to 100 wt. %, of a diphenol compound or a mixture of at least two diphenol compounds, having a spherical shape and a mean particle diameter $d_{50}$ of between 0.3 mm and 1 cm, and having a water content of less than 1000 ppm.

The invention further relates to diphenol prills comprising from 50 to 100 wt. %, preferably from 75 to 100 wt. %, and more preferably from 90 to 100 wt. %, of a mixture of at least two diphenol compounds, having a spherical shape and a mean particle diameter $d_{50}$ of between 0.3 mm and 1 cm.

The invention further relates to diphenol prills comprising from 50 to 99.9 wt. %, preferably from 60 to 99 wt. %, and more preferably from 75 to 90 wt. %, of a diphenol compound or a mixture of at least two diphenol compounds, and from 0.1 to 50 wt. %, preferably from 1 to 40 wt. %, and more preferably from 10 to 25 wt. %, of one or several other compounds, having a spherical shape and a mean particle diameter $d_{50}$ of between 0.3 mm and 1 cm.

Moreover, the invention relates to the use of said diphenol prills as antioxidant, polymerization inhibitor or as building block for the synthesis of organic or inorganic compound, for instance as a monomer for polymer production.

Another subject-matter of the present invention relates to a new form of a diphenol derivative of formula (IV)

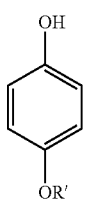

Formula (IV)

wherein R' represents an alkyl group or an aryl group. Specifically the present invention relates to a process for the preparation of prills of a diphenol derivative according to formula (IV), said process comprising:
- providing a molten composition comprising from 50 to 100 wt. %, preferably from 75 to 100 wt. % and more preferably from 90 to 100 wt. %, of the diphenol derivative compound, and less than 0.1 wt. % of water;
- forcing said molten composition through at least one droplet generator means to form droplets;
- cooling said droplets to form solid prills of the diphenol derivative.

DETAILED DESCRIPTION OF THE INVENTION

Figure 1:
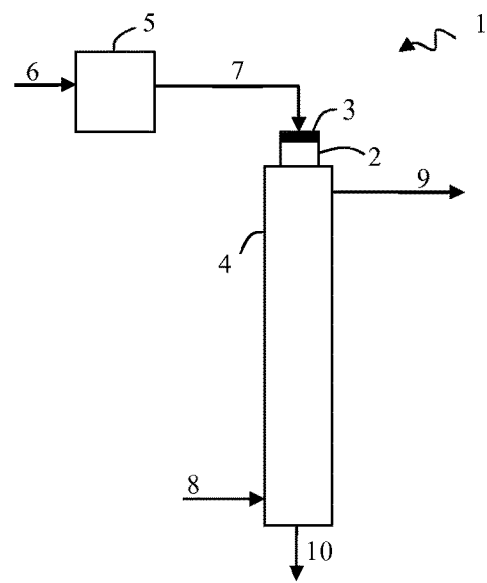
FIG. 1, FIG. 2 and FIG. 3 represent three different embodiments of a prilling device according to the invention.

In the present disclosure, the expression <<comprised between . . . and . . . >> should be understood has including the limits.

In a first aspect, the present invention relates to a process for the preparation of prills of compounds of formula (A)

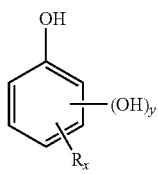

Formula (A)

wherein:
- y=0 or 1,
- R represents a substituent selected from the group consisting of an alkyl group, an alkenyl group, an alkoxy group, a hydroxyalkyl group, an alkoxyalkyl group, a cycloalkyl group, an aryl group, an aryloxy group, an arylalkyl group, a hydroxyl group, a nitro group, a halogen atom, a halo- or perhaloalkyl group, a formyl group, an acyl group, a carboxylic group, an amino group and an amido group
- x=0, 1, 2, 3 or 4 with the proviso that if y=0 then x=1 and R is an alkoxy group in para position to the hydroxyl group, said process comprising:

- providing a molten composition comprising from 50 to 100 wt. %, preferably from 75 to 100 wt. % and more preferably from 90 to 100 wt. %, of the diphenol derivative of formula (A) and less than 0.1 wt. % of water;
- forcing said molten composition through at least one droplet generator means to form droplets;
- cooling said droplets to form solid diphenol derivative prills.

One particular subject-matter of the present invention is a process for the preparation of diphenol prills.

In the present disclosure, "diphenol" means a chemical compound having at least one benzene cycle bearing at least two hydroxyl groups. Diphenol compound in the present invention is preferably a compound according to the general formula (I), (II) or (III)

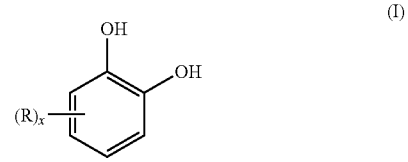

(I)

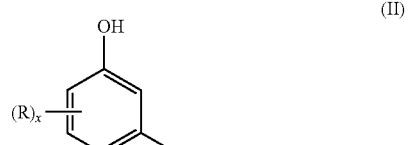

(II)

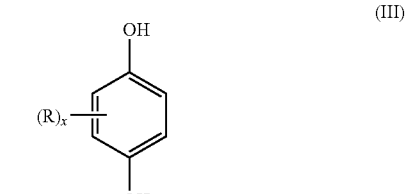

(III)

wherein x represents 0, 1, 2, 3 or 4, and each R independently represents a substituent selected from the group consisting of an alkyl group, an alkenyl group, an alkoxy group, a hydroxyalkyl group, an alkoxyalkyl group, a cycloalkyl group, an aryl group, an aryloxy group, an arylalkyl group, a hydroxyl group, a nitro group, a halogen atom, a halo- or perhaloalkyl group, a formyl group, an acyl group, a carboxylic group, an amino group and an amido group.

The following terms have their ordinary meaning.

Thus, in the present disclosure, "alkyl" refers to a linear or branched saturated hydrocarbon chain, having 1 to 15 carbon atoms, preferably 1 to 10 carbon atoms. Preferred examples of alkyl groups are methyl, ethyl, propyl, isopropyl, butyl, isobutyl and t-butyl.

"Alkenyl" refers to a linear or branched saturated hydrocarbon chain, having 2 to 15 carbon atoms, preferably 2 to 10 carbon atom, and having one or more double bonds. Preferred examples of alkenyl groups are ethenyl, propenyl, isopropenyl, butenyl, and isobutenyl.

"Alkoxy" refers to an alkyl-O— group, wherein alkyl has the meaning defined above. Preferred examples of alkoxy groups are methoxy and ethoxy.

"Cycloalkyl" refers to a monocyclic hydrocarbon chain, having 3 to 8 carbon atoms. Preferred examples of cycloalkyl groups are cyclopentyl and cyclohexyl.

"Aryl" refers to a monocyclic or polycyclic aromatic hydrocarbon group, having 6 to 20 carbon atoms. Preferred examples of aryl groups are phenyl and naphthyl. When the group is a polycyclic group, the rings may be condensed or attached by a (sigma) bonds.

"Aryloxy" refers to an aryl-O— group, wherein aryl has the meaning defined above. Preferred examples of aryloxy groups are phenoxy and naphthyloxy.

"Halogen atom" refers to fluorine, chlorine, bromine and iodine, preferably a chlorine or fluorine.

"Halo or perhaloalkyl" means one of the following groups: —$CX_3$, —$[CX_2]_p$—$CX_3$ or —$C_pH_aX_b$ in which said groups X represents a halogen atom, preferably a chlorine or fluorine atom; p represents a number ranging from 1 to 10, b a number ranging from 3 to 21 and a+b=2p+1.

The formula (I) represents diphenol compounds having hydroxyl groups in ortho position. The formula (II) represents diphenol compounds having hydroxyl groups in meta position. The formula (III) represents diphenol compounds having hydroxyl groups in para position. Preferably, diphenol compounds according to the present invention have hydroxyl groups in ortho position or in para position, i.e. may preferably be according to formula (I) or formula (III).

More preferably, a diphenol compound in the present invention may be a compound according to said general formula (I), (II) or (III), wherein x represents 0, 1, 2 or 3, especially x represents 0 or 1, and each R independently represents a substituent selected from the group consisting of an alkyl group, an alkoxy group and a hydroxyl group.

As illustrations of diphenol compounds, mention may be made of:
   those corresponding to formula (I), (II) or (III) in which x is zero, such as pyrocatechol, resorcinol and hydroquinone;
   those corresponding to formula (I), (II) or (III) in which x is 1, such as pyrogallol, 4-tert-butyl-catechol, tert-butyl-hydroquinone.

According to a specific embodiment, the diphenol compounds in the present invention may be selected from the group consisting of pyrocatechol (PC), hydroquinone (HQ), resorcinol (Res), pyrogallol (Py), 4-tert-butyl-catechol (TBC) and tert-butyl-hydroquinone (TBHQ), more preferably the diphenol compound is hydroquinone or a mixture of hydroquinone with at least one other diphenol compound.

Another particular aspect of the present invention is a process for the preparation of prills of a diphenol derivative of formula (IV)

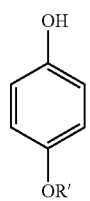

Formula (IV)

wherein R' represents an alkyl group or an aryl group, preferably R' represents methyl, ethyl, propyl, isopropyl, butyl, isobutyl and t-butyl or phenyl, said process comprising:
   providing a molten composition comprising from 50 to 100 wt. %, preferably from 75 to 100 wt. % and more preferably from 90 to 100 wt. %, of the diphenol derivative of formula (IV) and less than 0.1 wt. % of water;
   forcing said molten composition through at least one droplet generator means to form droplets;
   cooling said droplets to form solid diphenol derivative prills.

In this context, "alkyl" and "aryl" have the same meaning as previously described.

According to a specific embodiment, the diphenol derivative compounds in the present invention may be selected from the group consisting of para-methoxyphenol (PMP), para-ethoxyphenol (PEP), or para-phenoxyphenol (PPP).

The first step of the process according to the invention comprises providing a molten composition comprising from 50 to 100 wt. % of a diphenol compound or a mixture of at least two diphenol compounds, and less than 0.1 wt. % of water.

The content of diphenol(s) compound in said molten composition is preferably from 75 to 100 wt. %, and more preferably from 90 to 100 wt. %. Preferably, said molten composition may comprise from 50 to 100 wt. %, preferably from 75 to 100 wt. %, and more preferably from 90 to 100 wt. % of one diphenol compound selected from the group consisting of pyrocatechol, hydroquinone, resorcinol, 4-tert-butyl-catechol and tert-butyl-hydroquinone, or mixtures thereof. Very preferably, said molten composition may comprise from 50 to 100 wt. %, preferably from 75 to 100 wt. %, and more preferably from 90 to 100 wt. % of hydroquinone.

According to one embodiment, the molten composition in the invention consists in a highly pure diphenol composition, that is a diphenol composition comprising at least 98 wt. %, more preferably at least 99 wt. % of a diphenol compound, an even more preferably at least 99.5 wt. %, preferably of hydroquinone. However a highly pure hydroquinone composition may still comprise some impurities, preferably less 10000 ppm of total impurities, more preferably less than 5000 ppm of total impurities, and even more preferably less than 1000 ppm of total impurities.

According to another embodiment, the molten composition in the invention can comprise from 50 to 100 wt. %, preferably from 75 to 100 wt. %, and more preferably from 90 to 100 wt. %, of a mixture of at least two diphenol compounds. Mixtures of diphenols can be hydroquinone/resorcinol, hydroquinone/pyrogallol, hydroquinone/4-tert-butyl-catechol.

According to another embodiment, the molten composition in the invention can comprise from 50 to 99.9 wt. %, preferably from 60 to 99 wt. %, and more preferably from 75 to 90 wt. %, of a diphenol compound or a mixture of at least two diphenol compounds, and from 0.1 to 50 wt. %, preferably from 1 to 40 wt. %, and more preferably from 10 to 25 wt. %, of one or several other compounds. Other compounds may be any compound found suitable by the person skilled in the art, and it obviously does not include water. Preferred other compounds may have a melting point above 15° C. and/or solubility in water above 0.05% at 40° C. Preferred other compounds may be selected from the group consisting of:
   diphenol derivatives, especially diphenol ether, for instance para-methoxyphenol (PMP), para-phenoxyphenol (PPP), dibutylhydroxyanisole (BHA), 2,6-diter-tbutyl-4-methoxyphenol (DTBHA), vanillin, ethyl vanillin, vanillin alcohol, vanillic acid, and paradimethoxybenzene (PDMB);

phenol derivatives, especially alkylated phenols, for instance dibutylhydroxytoluene (BHT) and 2,4-dimethyl,6-tertbutyl-phenol (TOPANOL A);

other organic compounds, especially cyclic or heterocyclic compounds, for instance phenothiazine (PTZ), derivatives of TEMPO, preferably tetramethyl piperidinyloxy (TEMPO), hydroxyl-tetramethyl piperidinyloxy (TEMPO-OH), 4-oxo-2,2,6,6-tetramethyl-1-piperidinyloxyl (4-Oxo-TEMPO), benzoquinone (PBQ), benzoic acid.

In a particular aspect, the other compounds are selected from tocopherol derivatives, preferably α-tocopherol (Vitamin E), β-tocopherol, γ-tocopherol, δ-tocopherol, and complexes of copper having an oxidation state of 2, preferably copper dibutyl dithiocarbamate (CB) or copper acetate (Cu(OAc)$_2$), 2-sec-Butyl-4,6-dinitrophenol or p-phenylenediamine.

Other compounds may preferably be selected from the group consisting of para-methoxyphenol (PMP), para-phenoxy-phenol (PPP), dibutylhydroxytoluene (BHT), dibutylhydroxyanisole (BHA), 2,6-ditertbutyl-4-methoxyphenol (DTBHA), 2,4-dimethyl,6-tertbutyl-phenol (TOPANOL A), phenothiazine (PTZ). Copper dibutyl dithiocarbamate (CB) or copper acetate (Cu(OAc)$_2$), TEMPO and TEMPO-OH are also preferred other compounds.

According to a specific embodiment, said molten composition may comprise:

from 50 to 100 wt. %, preferably from 75 to 100 wt. % and more preferably from 90 to 100 wt. % of hydroquinone, and from 0 to 50 wt. %, preferably from 0 to 25 wt. %, and more preferably from 0 to 10 wt. %, of para-methoxyphenol, resorcinol, para-phenoxy-phenol, pyrocatechol, dibutylhydroxytoluene, tert-butyl-hydroquinone, 2,6-ditertbutyl-4-methoxyphenol and phenothiazine, or mixtures thereof.

Some preferred molten compositions are:

a composition of from 90 to 100 wt. % of hydroquinone and from 0 to 10 wt. %, of para-methoxyphenol;

a composition of from 90 to 100 wt. % of hydroquinone and from 0 to 10 wt. %, of para-phenoxy-phenol;

a composition of from 90 to 100 wt. % of hydroquinone and from 0 to 10 wt. %, of resorcinol;

a composition of from 90 to 100 wt. % of hydroquinone, from 0 to 5 wt. %, of para-methoxyphenol and from 0 to 5 wt. %, of para-phenoxy-phenol.

In another aspect of the present invention, the first step of the process according to the invention comprises providing a molten composition comprising from 50 to 100 wt. % of a diphenol derivative according to formula (IV) and less than 0.1 wt. % of water.

The content of diphenol derivative according to formula (IV) in said molten composition is preferably from 75 to 100 wt. %, and more preferably from 90 to 100 wt. %. Preferably, said molten composition may comprise from 50 to 100 wt. %, preferably from 75 to 100 wt. %, and more preferably from 90 to 100 wt. % of one diphenol derivative selected from the group consisting of PMP or PEP. Very preferably, said molten composition may comprise from 50 to 100 wt. %, preferably from 75 to 100 wt. %, and more preferably from 90 to 100 wt. % of PMP.

According to one embodiment, the molten composition in the invention consists in a highly pure diphenol derivative according to formula (IV), comprising at least 98 wt. %, more preferably at least 99 wt. % of a diphenol derivative according to formula (IV), an even more preferably at least 99.5 wt. %, preferably of PMP. However a highly pure PMP composition may still comprise some impurities, preferably less 10000 ppm of total impurities, more preferably less than 5000 ppm of total impurities, and even more preferably less than 1000 ppm of total impurities.

According to another embodiment, the molten composition in the invention can comprise from 50 to 99.9 wt. %, preferably from 60 to 99 wt. %, and more preferably from 75 to 90 wt. %, of a diphenol derivative according to formula (IV) and from 0.1 to 50 wt. %, preferably from 1 to 40 wt. %, and more preferably from 10 to 25 wt. %, of one or several other compounds. Other compounds may be any compound found suitable by the person skilled in the art, and it obviously does not include water. Preferred other compounds may have a melting point above 15° C. and/or solubility in water above 0.05% at 40° C. Preferred other compounds may be selected from the group consisting of:

diphenol derivatives, especially diphenol ether, for instance para-phenoxy-phenol (PPP), dibutylhydroxyanisole (BHA), 2,6-ditertbutyl-4-methoxyphenol (DTBHA), vanillin, ethyl vanillin, vanillin alcohol, vanillic acid, and paradimethoxybenzene (PDMB);

phenol derivatives, especially alkylated phenols, for instance dibutylhydroxytoluene (BHT) and 2,4-dimethyl,6-tertbutyl-phenol (TOPANOL A);

other organic compounds, especially cyclic or heterocyclic compounds, for instance phenothiazine (PTZ), derivatives of TEMPO, preferably tetramethyl piperidinyloxy (TEMPO), hydroxyl-tetramethyl piperidinyloxy (TEMPO-OH), 4-oxo-2,2,6,6-tetramethyl-1-piperidinyloxyl (4-Oxo-TEMPO), benzoquinone (PBQ), benzoic acid.

In a particular aspect, the other compounds are selected from tocopherol derivatives, preferably α-tocopherol (Vitamin E), β-tocopherol, γ-tocopherol, δ-tocopherol, and complexes of copper having an oxidation state of 2, preferably copper dibutyl dithiocarbamate (CB) or copper acetate (Cu(OAc)$_2$), 2-sec-Butyl-4,6-dinitrophenol or p-phenylenediamine.

Other compounds may preferably be selected from the group consisting of para-phenoxy-phenol (PPP), dibutylhydroxytoluene (BHT), dibutylhydroxyanisole (BHA), 2,6-ditertbutyl-4-methoxyphenol (DTBHA), 2,4-dimethyl,6-tertbutyl-phenol (TOPANOL A), phenothiazine (PTZ), copper dibutyl dithiocarbamate (CB) or copper acetate (Cu(OAc)$_2$), TEMPO, TEMPO-OH and α-tocopherol.

According to a specific embodiment, said molten composition may comprise:

from 50 to 100 wt. %, preferably from 75 to 100 wt. % and more preferably from 90 to 100 wt. % of PMP, and from 0 to 50 wt. %, preferably from 0 to 25 wt. %, and more preferably from 0 to 10 wt. %, of phenothiazine, α-tocopherol (Vitamin E), 2-sec-Butyl-4,6-dinitrophenol, p-phenylenediamine or mixtures thereof.

Some preferred molten compositions are:

a composition of from 90 to 100 wt. % of PMP and from 0 to 10 wt. %, of α-tocopherol (Vitamin E);

a composition of from 50 to 60 wt. % of PMP and from 40 to 50 wt. %, of α-tocopherol (Vitamin E).

Moreover, said molten composition may further comprise at least one additive selected from the group consisting of antioxidants, antifoams, rust inhibitors, corrosion inhibitors, surfactants, detergents, dispersants, antifouling additives, and anti-deposition agents.

The molten composition according to the invention comprises less than 0.1 wt. % of water. Therefore, said composition is not an aqueous solution.

Said composition is said to be in a molten form, which means that it is liquid enough to flow into the process devices. In the present description, a compound can be considered to be liquid when its viscosity is advantageously less than or equal to 100 Pa·s, preferably 1 Pa·s, and more preferably 10 mPa·s, measured by means of a Rheomat 30 viscometer for shear rates of 100 $s^{-1}$ to 500 $s^{-1}$. The composition may need to be heated so as to be in a molten form. The duration and temperature of heating are adapted according to the composition. Preferably, the composition according to the invention is heated to a temperature of 1° C. to 20° C. above the melting point of the composition, preferably 1° C. to 10° C. above the melting point. Said temperature may typically be between 50° C. and 260° C. Preferably, said temperature may typically be between 50° C. and 200° C. The molten composition may be at least temporary stocked into a tank provided with a system for regulating the temperature, for example a jacket, to maintain said compound in liquid form.

The second step of the process according to the invention comprises forcing said molten composition through at least one droplet generator means to form droplets. The droplet generator means may be any fragmentation device, for example a turbine, a spray nozzle, or a flat nozzle with orifice(s).

The nozzle used can be a single- or multi-holed nozzle with a number of holes which can be from 1 to 3000 holes, preferably between 1 and 100 holes. It is possible to use a system comprising a plurality of nozzles, for example 2 nozzles, preferably removable, in parallel. The diameter of the nozzle perforations is a function of the desired prill size. It may be 100 to 1500 nm, but is preferably between 200 µm and 600 nm.

According to one embodiment, the nozzle used can be a static nozzle, but it is possible to use a nozzle subjected to a vibrating means applying a frequency of between 10 and 10 000 Hz. That device can advantageously produce droplets with a perfectly calibrated size.

The molten composition is fed to the droplet generator means preferably at an overpressure ensured by a stream of gas, preferably a stream of nitrogen. The overpressure with respect to the atmospheric pressure is 5% to 500%. Preferably, the temperature in the droplet generator is 1° C. to 20° C. above the melting point.

The droplet generator means is preferably maintained at a temperature equal to or above the temperature at which the composition is in a molten form.

The third step of the process according to the invention comprises cooling said droplets to form solid diphenol prills.

According to another aspect of the present invention, the third step of the process according to the invention comprises cooling said droplets to form solid prills of diphenol derivative according to formula (IV).

According to a first embodiment, the cooling may be carried out by a cooling medium which is a cooling gas, preferably an inert gas, more preferably depleted air or nitrogen, at a temperature of between −196° C. and +100° C., preferably between −40° C. and +30° C., and more preferably between −20° C. and 20° C. In this text, "depleted air" means oxygen-depleted air, for instance air comprising less than 10% of oxygen. It is not excluded that the cooling gas can be air.

Preferably, the cooling medium flows counter-currently with respect to the droplets of the diphenol composition. The cold gas stream preferably leaves the tower below the nozzle at a distance representing about one tenth of the total height of the cooling zone.

The residence time, namely the period between formation of the droplet at the nozzle outlet and its arrival in the recovery system is advantageously between 0.1 second and 10 seconds, more preferably between 0.5 second and 3 seconds.

According to a second embodiment, the cooling may be carried out by a cooling medium which is a liquefied inert gas, preferably liquid nitrogen.

Said cooling medium may preferably flow co-currently with respect to the droplets of the diphenol composition. It may advantageously be introduced at the top of the cooling tower, near the droplet generator means, by the means of a liquid nitrogen spray ring.

According to a third embodiment, the cooling may be carried out by two cooling media: the droplets may be first cooled by a liquefied inert gas, preferably liquid nitrogen, and secondly by a cooling gas. Said liquefied inert gas and said cooling gas may preferably be as defined in the first and second embodiments above. Without wishing to be bound by any theory, it is believed that the liquefied inert gas may first solidify at least a fraction of the droplets, whereas the cooling gas may secondly complete the solidification of the droplets to obtain prills, which have a sufficiently solidified outer shell to withstand physical impacts on equipment, or collisions with other prills in a fluidized bed.

According to a fourth embodiment, the cooling may be carried out by two cooling media: the droplets may be first cooled by an inert gas, and secondly by a second cooling gas in another cooling part. The first and the second cooling gas may preferably be as defined in the first and second embodiment. The temperature of the second cooling gas is preferably higher than the temperature of the first cooling gas. Preferably the temperature of the first cooling gas is between −20° C. and +10° C., and the temperature of the second cooling gas is between +10° C. and +30° C.

At the end of the cooling step, solid diphenol prills are obtained. They may be recovered using any known means, for example under gravity in a recovery vessel or using the fluidized bed technique.

At the end of the cooling step, solid prills of diphenol derivative according to formula (IV) are obtained. They may be recovered using any known means, for example under gravity in a recovery vessel or using the fluidized bed technique.

Independently to the prilling method, the solid diphenol prills or solid diphenol derivative prills are converted from a molten composition to solid prills of diphenol or of diphenol derivative with a conversion yield of higher than or equal to 70%, preferably higher than or equal to 80%, more preferably higher than or equal to 90% and still more preferably higher than or equal to 99%. In a specific aspect of the invention the conversion yield of the molten composition to the prills is quantitative. The conversion yield can be defined as the ratio between the weight of prills formed and the weight of the molten composition.

At the end of the process according to the invention, the amount of fines particles having a size of less than 355 µm is lower or equal to 30%, preferably lower or equal to 20%, more preferably lower or equal to 10%, still more preferably lower or equal to 1%, and even still more preferably lower or equal to 0.1% by weight of the total weight of the molten composition. Advantageously, at the end of the process according to the invention, the amount of fines particles having a size of less than 100 µm is lower or equal to 30%, preferably lower or equal to 20%, more preferably lower or equal to 10%, still more preferably lower or equal to 1% and even still more preferably lower or equal to 0.1% by weight of the total weight of the molten composition. The amount of fine particles is measured at the outlet of the prilling tower before any fine particles are separated.

The apparatus used to carry out the process of the invention may be called a priller device.

One embodiment of the invention is represented on FIG. 1.

On FIG. 1, the priller device (1) comprises a droplet generator means (2) and a prilling tower (4). The droplet generator means (2) is provided with a vibrating means (3). The molten composition according to the invention is stocked in a heated tank (5), which maintains the composition in a molten state. A gas stream (6) (typically nitrogen) is provided to the tank (5) so that the molten composition (7) is fed to the droplet generator (3). Droplets of the molten composition fall into the prilling tower (4).

The cooling gas (8) is introduced at the bottom of the tower (4), flows counter-currently with respect to the droplets of the diphenol composition, and leaves the tower at point (9) below droplet generator means (2). At the lower portion of the prilling tower (4), the prills (10) are collected.

The prilling tower (4) may be provided with any means which are typically used to allow a homogeneous distribution of the gas stream, for example baffles and screens (not shown).

According to this configuration, the upper part of the prilling tower (4) is configured for forming the prills, whereas the lower part is configured for entirely solidifying and for recovering the prills. The height of the tower (4) can vary widely, and can be determined by the skilled people according to thermal mass balance of the installation, typically between 1 and 50 meters depending on the size of the facility.

Figure 2:
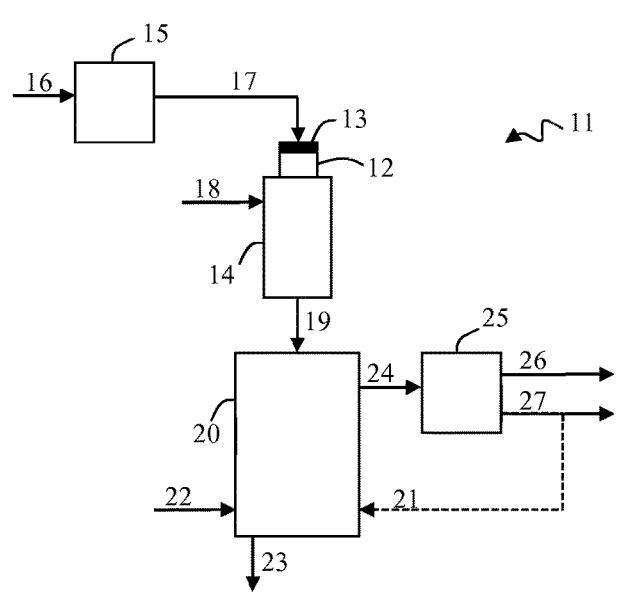

Another embodiment of the invention is represented on FIG. 2.

On FIG. 2, the priller device (11) comprises a droplet generator means (12) and a prilling tower (14). The droplet generator means (12) is provided with a vibrating means (13). The molten composition according to the invention is stocked in a heated tank (15), which maintains the composition in a molten state. A gas stream (16) (typically nitrogen) is provided to the tank (15) so that the molten composition (17) is fed to the droplet generator (12). Droplets of the molten composition fall into the prilling tower (14).

The cooling medium, which is liquid nitrogen (18) is introduced at the top of the tower (14), near the droplet generator means (12). It flows co-currently with respect to the droplets of the diphenol composition. At the lower portion of the prilling tower (14), the diphenol prills (19) are collected and sent to a spiral cooler (20), wherein the solidification of the prills is completed in a fluidized bed with a countercurrent cold gaseous nitrogen stream. Said cold nitrogen stream is introduced at the bottom of the spiral cooler (20) by recycling of the nitrogen used in the prilling tower (21) and/or by fresh cold nitrogen (22).

At the lower portion of the spiral cooler (20), the prills (23) are collected.

Optionally, the gaseous nitrogen stream is removed on top (24) of the spiral cooler, together with some fine material. A cyclone (25) may be used for separating fines (26) and nitrogen (27). Nitrogen may optionally be recycled in the spiral cooler (20).

Figure 3:
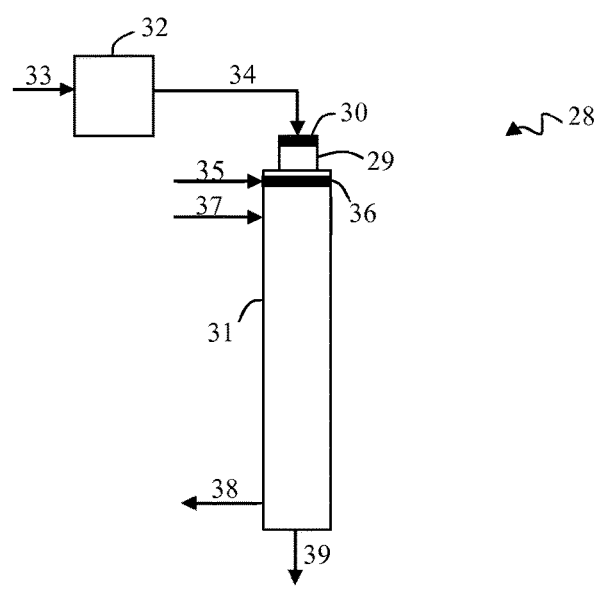

Another embodiment of the invention is represented on FIG. 3.

On FIG. 3, the priller device (28) comprises a droplet generator means (29) and a prilling tower (31). The droplet generator means (29) is provided with a vibrating means (30). The molten composition according to the invention is stocked in a heated tank (32), which maintains the composition in a molten state. A gas stream (33) (typically nitrogen) is provided to the tank (32) so that the molten composition (34) is fed to the droplet generator (29). Droplets of the molten composition fall into the prilling tower (31).

A first cooling medium, which is liquid nitrogen (35) is introduced at the top of the tower (31), near the droplet generator means (29), by the means of a liquid nitrogen spray ring (36). Said cooling medium may solidify at least a fraction of the droplets. A second cooling medium (37), which may typically be cold nitrogen stream, is introduced in the tower (31), flows co-currently with respect to the droplets of the diphenol composition, and leaves the tower at the bottom of the tower (38). Said second cooling medium is requested to complete the solidification of the droplets to obtain prills, which have a sufficiently solidified outer shell to withstand physical impacts on equipment, or collisions with other prills in a fluidized bed. At the lower portion of the prilling tower (31), the prills (39) are collected. Said diphenol prills may be further sent to an additional cooling means (not showed); like the spiral cooler represented on FIG. 2.

The process according to the invention may further comprise a step comprising separating fine particles by sieving or cycloning, and recycling the said fine particles. The size of the fine particles separated being less than 355 μm.

Preferably, the process according to the invention may further comprise a step comprising separating fine particles of diphenol prills having a size of less than 100 μm, preferably by sieving or cycloning, and recycling said fine particles.

In another aspect of the present invention, the process according to the invention may further comprise a step comprising separating fine particles of prills of diphenol derivative according to formula (IV) having a size of less than 100 μm, preferably by sieving or cycloning, and recycling said fine particles.

The diphenol prills obtainable or obtained by said process are also one subject-matter of the present invention.

The prills of diphenol derivatives according to formula (IV) obtainable or obtained by said process are also one subject-matter of the present invention.

Additionally, the invention relates to diphenol prills comprising from 50 to 100 wt. %, preferably from 75 to 100 wt. %, and more preferably from 90 to 100 wt. %, of a diphenol compound or a mixture of at least two diphenol compounds, having a spherical shape and a mean particle diameter $d_{50}$ of between 0.3 mm and 1 cm, and having a water content of less than 1000 ppm. The water content may be of strictly less than 1000 ppm, meaning that 1000 ppm is excluded. The water content may be of less than 999 ppm, or of less than 900 ppm.

The invention further relates to diphenol prills comprising from 50 to 100 wt. %, preferably from 75 to 100 wt. %, and more preferably from 90 to 100 wt. %, of a mixture of at least two diphenol compounds, having a spherical shape and a mean particle diameter $d_{50}$ of between 0.3 mm and 1 cm.

The invention further relates to diphenol prills comprising from 50 to 99.9 wt. %, preferably from 60 to 99 wt. %, and more preferably from 75 to 90 wt. %, of a diphenol compound or a mixture of at least two diphenol compounds, and from 0.1 to 50 wt. %, preferably from 1 to 40 wt. %, and more preferably from 10 to 25 wt. %, of one or several other compounds, having a spherical shape and a mean particle diameter $d_{50}$ of between 0.3 mm and 1 cm.

In the present description, "prills" is used to define solid substantially spherical particles. "Substantially spherical" means that it has high sphericity and is not necessarily required to be perfectly spherical. Although the prills according to the present invention can be considered as spherical, it may contain "blow holes".

The mean particle diameter $d_{50}$ is defined as being such that 50% by mass of the particles have a diameter greater or less than the median diameter. The particle size analysis is performed on a Malvern Mastersizer 3000 laser granulometer in wet or dry mode (Scirocco dispersion of the dry particles) or directly by micrometer screw gauge. The mean particle diameter $d_{50}$ of the diphenol prills according to the invention is of between 0.3 mm and 1 cm, preferably of between 0.4 mm and 5 mm, more preferably of between 0.5 mm and 3 mm, more preferably between 0.8 mm and 2 mm.

Advantageously, the diphenol prills according to the invention show a high hardness and a low friability.

Preferably, diphenol prills according to the invention have a hardness of at least 1 N. The hardness of the prills may be measured with a penetrometer.

Additionally, the diphenol prills according to the invention may advantageously have a friability of less than 15%. This characteristic of the diphenol prills according to the present invention allow a comparable or better handling of the diphenol prills in the application medium as the formation of fog of fine particles is avoided or at least reduced. The friability of the prills may be measured by mixing the prills in a triaxial mixer during ten minutes, and measuring the percentage of fines particles (i.e. particles of less than 100 μm) produced. The friability is calculated as the ratio of the mass of the fine particles produced over the mass of the prills introduced in the triaxial mixer.

The diphenol prills according to the invention may have good dissolution properties. The dissolution speed of these new prills may be as close as possible, preferably at least equivalent, or advantageously better, than the dissolution speed of other existing form of diphenol, for instance powder. At least, the dissolution speed of the new diphenol prills according to the invention is in accordance with the final user's needs. By way of illustration, the rate of dissolution at 20° C. for a concentration of 2% by weight of hydroquinone prills according to the invention in acrylic acid is of between 5 minutes and 120 minutes. The dissolution rate may be measured according to the following protocol: 2 g of prills are put into 100 g of acrylic acid at 20° C. and are agitated at 300 rpm with a glass propeller. It is considered that the prills are dissolved when 90% of the prills have disappeared.

Diphenol prills according to the invention may preferably have a color ranging from white to grey, preferably white. The color may be measured experimentally or visually assessed.

The chemical composition of the diphenol prills according to the invention depends on the chemical composition of molten composition as defined above. Advantageously, the present method does not require any processing agent, contrary to some prior art methods. Therefore, the final composition does not comprise any trace of said processing agent. The diphenol prills according to the present invention contain less than 1000 ppm of water. Moreover, the diphenol prills according to the invention do not contain water and do not require any drying step.

According to one specific embodiment, the diphenol prills according to the invention are highly pure diphenol prills, comprising at least 98 wt. %, more preferably at least 99 wt. % of a diphenol compound, an even more preferably at least 99.9 wt. %, preferably of hydroquinone.

According to another specific embodiment, the diphenol prills according to the invention may comprise:
  from 50 to 100 wt. %, preferably from 75 to 100 wt. % and more preferably from 90 to 100 wt. % of hydroquinone, and
  from 0 to 50 wt. %, preferably from 0 to 25 wt. %, and more preferably from 0 to 10 wt. %, of para-methoxyphenol, resorcinol, para-phenoxy-phenol, pyrocatechol, dibutylhydroxytoluene, tert-butyl-hydroquinone, 2,6-ditertbutyl-4-methoxyphenol phenothiazine, or mixtures thereof. In another aspect, the diphenols prills may comprise from 0 to 50 wt. %, preferably from 0 to 25 wt. %, and more preferably from 0 to 10 wt. %, of copper dibutyl dithiocarbamate (CB), TEMPO, 2-sec-Butyl-4,6-dinitrophenol, p-phenylenediamine or mixtures thereof.

Some preferred diphenol prills are:
  diphenol prills comprising from 90 to 100 wt. % of hydroquinone and from 0 to 10 wt. %, of para-methoxyphenol;
  diphenol prills comprising from 90 to 100 wt. % of hydroquinone and from 0 to 10 wt. %, of para-phenoxy-phenol;
  diphenol prills comprising from 90 to 100 wt. % of hydroquinone and from 0 to 10 wt. %, of resorcinol;
  diphenol prills comprising from 90 to 100 wt. % of hydroquinone, from 0 to 5 wt. %, of para-methoxyphenol and from 0 to 5 wt. %, of para-phenoxy-phenol,
  diphenol prills comprising from 75 to 100 wt %, preferably from 85 to 98 wt % of hydroquinone and from 0 to 25 wt % preferably from 2 to 15 wt % of copper dibutyl dithiocarbamate (CB),
  diphenol prills comprising from 75 to 90 wt % of hydroquinone and from 10 to 25 wt % or phenothiazine, According to another specific embodiment, the prills of a diphenol derivative according to formula (IV) according to the invention are highly pure diphenol derivative prills, that is diphenol derivative prills comprising at least 98 wt. %, more preferably at least 99 wt. % of a diphenol derivative of formula (IV), an even more preferably at least 99.9 wt. %, preferably of para-methoxyphenol.

According to another specific embodiment, the diphenol derivative prills according to the invention may comprise:
  from 50 to 100 wt. %, preferably from 75 to 100 wt. % and more preferably from 90 to 100 wt. % of para-methoxyphenol, and
  from 0 to 50 wt. %, preferably from 0 to 25 wt. %, and more preferably from 0 to 10 wt. %, of phenothiazine, α-tocopherol (Vitamin E), 2-sec-butyl-4,6-dinitrophenol, p-phenylenediamine or mixtures thereof.

Some preferred diphenol prills are:
  diphenol prills comprising from 90 to 100 wt. % of para-methoxyphenol and from 0 to 10 wt. %, of α-tocopherol;
  diphenol prills comprising from 50 to 60 wt. % of para-methoxyphenol and from 40 to 50 wt. %, of α-tocopherol.

In any case, diphenol prills according to the invention may further comprise at least one additive selected from the group consisting of antioxidants, antifoams, rust inhibitors, corrosion inhibitors, surfactants, detergents, dispersants, antifouling additives, and anti-deposition agents. If any, the additives may be added to the initial molten composition, or added to the final prills in a finishing step.

Finally, the invention relates to the use of said diphenol prills as antioxidant, polymerization inhibitor or as building block for the synthesis of organic or inorganic compound, for instance as a monomer for polymer production.

In another aspect, the invention relates to the use of said diphenol derivative prills as antioxidant, polymerization inhibitor or as building block for the synthesis of organic or inorganic compound.

The disclosure of all patent applications, and publications cited herein are hereby incorporated by reference, to the extent that they provide exemplary, procedural or other details supplementary to those set forth herein. Should the disclosure of any of the patents, patent applications, and publications that are incorporated herein by reference conflict with the present specification to the extent that it might render a term unclear, the present specification shall take precedence.

Each and every claim is incorporated into the specification as an embodiment of the present invention. Thus, the claims are a further description and are an addition to the preferred embodiments of the present invention.

While preferred embodiments of this invention have been shown and described, modifications thereof can be made by one skilled in the art without departing from the spirit or teaching of this invention. The embodiments described herein are exemplary only and are not limiting. Many variations and modifications of systems and methods are possible and are within the scope of the invention.

Accordingly, the scope of protection is not limited by the description and Examples set out below, but is only limited by the claims which follow, that scope including all equivalents of the subject matter of the claims.

EXAMPLES

A laboratory prilling device was used to produce laboratory scale prills. The laboratory prilling device comprises a glass reactor heated with silicone oil. At the bottom of the reactor is fixed a needle valve with adjusted and stabilized dripping, which generates droplets, and which is connected to liquid nitrogen bath. Droplets formed by the needle valve may fall and solidify into the nitrogen bath, and the obtained prills may be collected with a sieve.

Example 1: Preparation of Hydroquinone Prills

Pure hydroquinone (containing more than 99.9 wt. % of hydroquinone, and less than 600 ppm of water) was fed in the glass reactor, and the temperature was set at 200° C. so that hydroquinone was kept in the molten form. Hydroquinone prills were produced with the laboratory prilling device.

Figure 4:
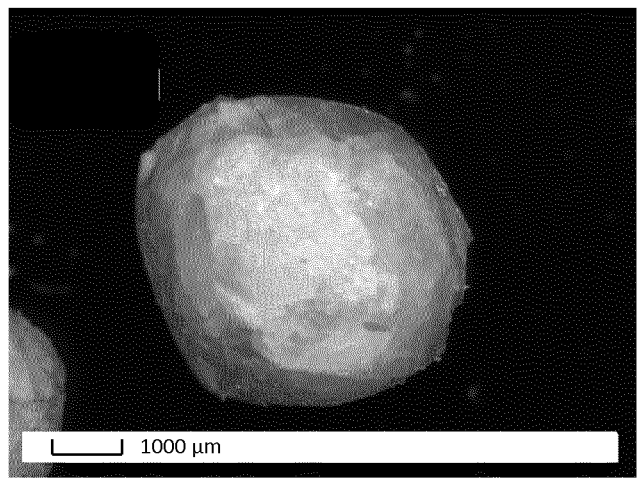
FIG. 4 and FIG. 5 are microscopic views of hydroquinone prills obtained according to respectively Example 1 and Example 2.

The hydroquinone prills are shown in FIG. 4. Advantageously, said prills are highly spherical.

Examples 2-13: Preparation of Various Diphenol Prills

Figure 5:
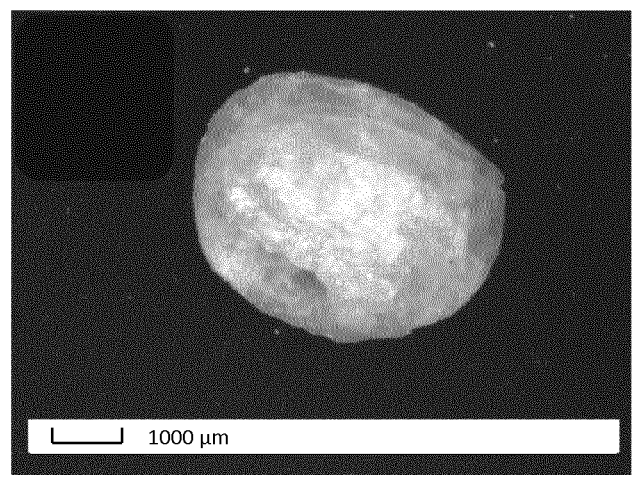

The Example 1 was reproduced with several diphenol compositions:

Ex.2: 95 wt. % hydroquinone, 5 wt. % para-methoxyphenol (the prills are shown in FIG. 5)
Ex.3: 97 wt. % hydroquinone, 3 wt. % para-methoxyphenol
Ex.4: 99 wt. % hydroquinone, 1 wt. % para-methoxyphenol
Ex.5: 95 wt. % hydroquinone, 5 wt. % pyrocatechol
Ex.6: 99 wt. % hydroquinone, 1 wt. % pyrocatechol
Ex.7: 95 wt. % hydroquinone, 5 wt. % phenothiazine
Ex.8: 98 wt. % hydroquinone, 2 wt. % para-phenoxyphenol
Ex.9: 98 wt. % hydroquinone, 2 wt. % resorcinol
Ex.10: 99.4 wt. % hydroquinone, 0.5 wt % para-methoxyphenol, 0.1 wt. % para-phenoxy-phenol.
Ex 11: 98 wt. % hydroquinone, 2 wt. % para-methoxyphenol
Ex 12: 95 wt % hydroquinone, 5 wt % copper dibutyl dithiocarbamate,
Ex 13: 60 wt % paramethoxyphenol, 40 wt % α-tocopherol.

For each composition, spherical prills have been obtained.

Example 14: Properties

Several properties of the hydroquinone prills obtained according to Example 4 have been determined, according to the following methods:

Mean particle diameter: measured by micrometer screw gauge
Hardness: measured by penetrometer
Friability: percentage of fines particles (i.e. particles of less than 100 μm) produced after mixing in triaxial mixer during ten minutes.
Dissolution rate: time of dissolution of 90% of 2 g of prills in 100 g of acrylic acid at 20° C. agitated at 300 rpm with a glass propeller.
Caking/Clumping: visual assessment after storage during 7 days at 35° C.

The properties of the hydroquinone prills according to the invention are summarized in table 1, and are compared to some properties of other commercially available hydroquinone solid forms:

TABLE 1

|  | Prills of Ex.4 | HQ powder[1] | HQ flakes[2] |
|---|---|---|---|
| Mean particle diameter $d_{50}$ (mm) | 4 | 0.3 |  |
| % of particles <1 mm | <1% | >90% | >3% |
| Hardness (N) | 10 | Not relevant |  |
| Friability (%) | 3% | Not relevant |  |
| Dissolution rate (minutes) | 80 | 10 | 28 |
| Caking/Clumping | No | No |  |

[1]: commercial ref. of HQ powder
[2]: commercial ref. of HQ flakes

Example 15: Industrial Process

A prilling device as described in FIG. 1 has been used. The products were melted in a heated tank at a temperature of around 250° C.

For each composition, highly spherical prills were obtained. The properties of the prills are displayed in table 2.

TABLE 2

|  | 100% HQ | 100% HQ | 100% HQ | 99% HQ/1% PMP |
|---|---|---|---|---|
| Cooling temperature | −20° C. | 10° C. | 10° C. | 10° C. |
| Nozzle diameter (μm) | 500 | 500 | 700 | 500 |
| Mean particle diameter $d_{50}$ (mm) | 1 | 1 | 1.4 | 1 |

TABLE 2-continued

| | 100% HQ | 100% HQ | 100% HQ | 99% HQ/1% PMP |
|---|---|---|---|---|
| % of fine particles <300 μm (visual inspection, before fine particles removal) | <10 | <10 | <10 | <10 |
| Hardness (N) | >1 | >1 | >1 | >1 |
| Friability (%) | 2 | 1 | 1 | 1 |
| Dissolution rate (minutes) | 20-30 | 20-30 | 20-30 | >20 |

Figure 6:
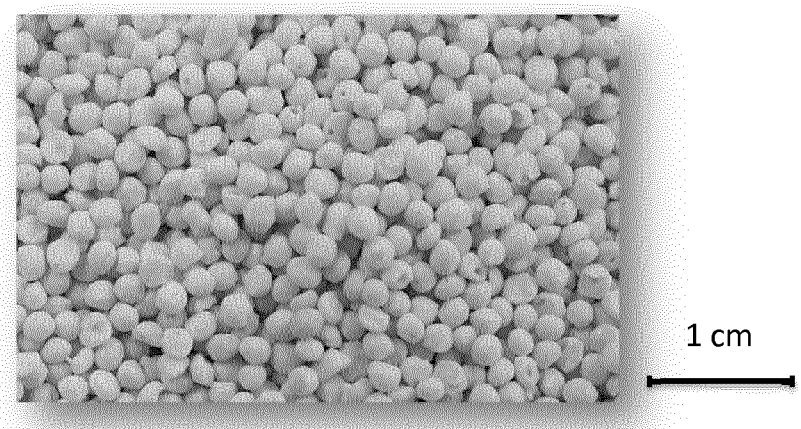
FIG. 6 is a photography of hydroquinone prills obtained on a small scale asset according to Example 15.

FIG. 6 shows a prill of HQ obtained in this prilling device.

The invention claimed is:

1. A process for the preparation of prills of one or more compounds of formula (A):

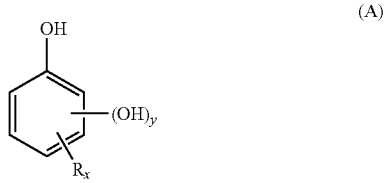

wherein:
y=0 or 1,
R represents a substituent selected from the group consisting of an alkyl group, an alkenyl group, an alkoxy group, a hydroxyalkyl group, an alkoxyalkyl group, a cycloalkyl group, an aryl group, an aryloxy group, an arylalkyl group, a hydroxyl group, a nitro group, a halogen atom, a halo- or perhaloalkyl group, a formyl group, an acyl group, a carboxylic group, an amino group and an amido group,
x=0, 1, 2, 3 or 4,
with the proviso that if y=0, then x=1 and R is an alkoxy or aryloxy group in para position to the hydroxyl group,
said process comprising:
forcing a molten composition comprising from 50 to 100 wt. % of one or more compounds of formula (A) and less than 0.1 wt. % of water through at least one droplet generator means to form droplets; and
cooling said droplets to form solid prills.

2. The process according to claim 1, wherein y is 0.

3. The process according to claim 2, wherein the compound according to formula (A) is selected from the group consisting of para-methoxyphenol, para-ethoxyphenol, and para-phenoxyphenol.

4. The process according to claim 2, wherein said molten composition further comprises from 0 to 50 wt. % of one or more compounds selected from the group consisting of:
diphenol derivatives;
phenol derivatives; and
other organic compounds.

5. The process according to claim 4, wherein said molten composition comprises:
from 50 to 100 wt. % of para-methoxyphenol, and
from 0 to 50 wt. % of one or more compounds selected from the group consisting of phenothiazine, α-tocopherol, 2-sec-butyl-4,6-dinitrophenol, p-phenylenediamine, and mixtures thereof.

6. The process according to claim 1, wherein said molten composition further comprises at least one additive selected from the group consisting of antioxidants, antifoams, rust inhibitors, corrosion inhibitors, surfactants, detergents, dispersants, antifouling additives, and anti-deposition agents.

7. The process according to claim 1, wherein the cooling is carried out by a cooling medium which is a liquefied inert gas and said cooling medium flows co-currently with respect to the droplets of the diphenol composition.

8. The process according to claim 1, wherein the cooling is carried out by a cooling medium which is a cooling gas, at a temperature of between −40° C. and +100° C., and said cooling medium flows counter-currently with respect to the droplets of the diphenol composition.

9. The process according to claim 1, wherein the cooling comprises cooling the droplets by a liquefied inert gas and cooling the droplets by a cooling gas.

10. The process according to claim 1, further comprising a step comprising separating fine particles of diphenol prills having a size of less than 100 μm.

11. The process according to claim 1, wherein the one or more compounds of formula (A) are each selected from the group consisting of compounds according to formula (I), compounds according to formula (II), and compounds according to formula (III):

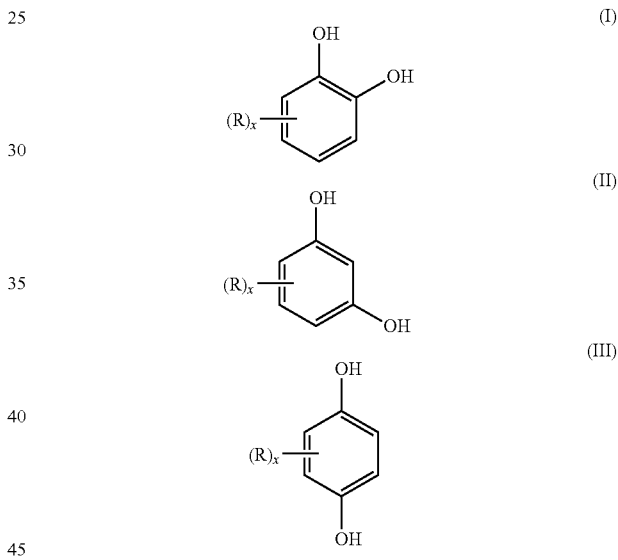

wherein x represents 0, 1, 2, 3, or 4, and each R independently represents a substituent selected from the group consisting of an alkyl group, an alkenyl group, an alkoxy group, a hydroxyalkyl group, an alkoxyalkyl group, a cycloalkyl group, an aryl group, an aryloxy group, an arylalkyl group, a hydroxyl group, a nitro group, a halogen atom, a halogeno- or perhalogenoalkyl group, a formyl group, an acyl group, a carboxylic group, an amino group, and an amido group.

12. The process according to claim 1, wherein the one or more compounds of formula (A) are each selected from the group consisting of pyrocatechol, hydroquinone, resorcinol, pyrogallol, 4-tert-butyl-catechol, tert-butyl-hydroquinone, and mixtures thereof.

13. The process according to claim 1, wherein said molten composition further comprises from 0 to 50 wt. % of one or more compounds selected from the group consisting of para-methoxyphenol, para-phenoxy-phenol, dibutylhydroxyanisole, 2,6-ditertbutyl-4-methoxyphenol, vanillin, ethyl vanillin, vanillin alcohol, vanillic acid, paradimethoxybenzene, dibutylhydroxytoluene, 2,4-dimethyl-6-tertbutylphenol, phenothiazine, tetramethyl piperidinyloxy, hydroxyl-tetramethyl piperidinyloxy, 4-oxo-2,2,6,6-tetramethyl-1-piperidinyloxyl, benzoquinone, and benzoic acid.

14. The process according to claim 13, wherein said molten composition comprises:
   from 50 to 100 wt. % of hydroquinone, and
   from 0 to 50 wt. % of one or more compounds selected from the group consisting of para-methoxyphenol, resorcinol, para-phenoxy-phenol, pyrocatechol, dibutylhydroxytoluene, tert-butyl-hydroquinone, 2,6-ditertbutyl-4-methoxyphenol, phenothiazine, and mixtures thereof.

15. The process according to claim 1, wherein said molten composition further comprises from 0 to 50 wt. % of one or more compounds selected from the group consisting of α-tocopherol, β-tocopherol, γ-tocopherol, δ-tocopherol, complexes of copper having an oxidation state of 2; 2-sec-butyl-4,6-dinitrophenol, and p-phenylenediamine.

\* \* \* \* \*